United States Patent [19]

Bockowski

[11] Patent Number: 5,271,819
[45] Date of Patent: Dec. 21, 1993

[54] METHOD OF DETECTION USING SENSOR ELECTRODE
[75] Inventor: Edmund J. Bockowski, Furlong, Pa.
[73] Assignee: Betz Laboratories, Inc., Trevose, Pa.
[21] Appl. No.: 889,927
[22] Filed: Jun. 2, 1992
[51] Int. Cl.⁵ ............................................ G01N 27/26
[52] U.S. Cl. ................................. 204/402; 204/409; 204/153.1; 134/22.12
[58] Field of Search ............... 204/402, 409, 129.1, 204/153.1; 134/22.12

[56] References Cited
U.S. PATENT DOCUMENTS

| 4,609,874 | 9/1986 | Reich | 204/409 |
| 5,051,193 | 9/1991 | Cummings, Jr. | 134/22.12 |
| 5,114,596 | 5/1992 | Laterra | 134/22.12 |

OTHER PUBLICATIONS

Zief and Kiser, An Overview of Solid Phase Extraction for Sample Preparation, Jan. 1990, pp. 70-83.

Primary Examiner—Donald R. Valentine
Assistant Examiner—Bruce F. Bell
Attorney, Agent, or Firm—Alexander D. Ricci; Gregory M. Hill

[57] ABSTRACT

A sensor electrode and method for detecting select characteristic in a liquid. The method utilizes filters and adsorbent materials to selectively remove contaminants in the liquid. The improvement comprises back flushing the filters and adsorbent material, once they become saturated, with specific solutions to wash away the select contaminants.

1 Claim, 2 Drawing Sheets

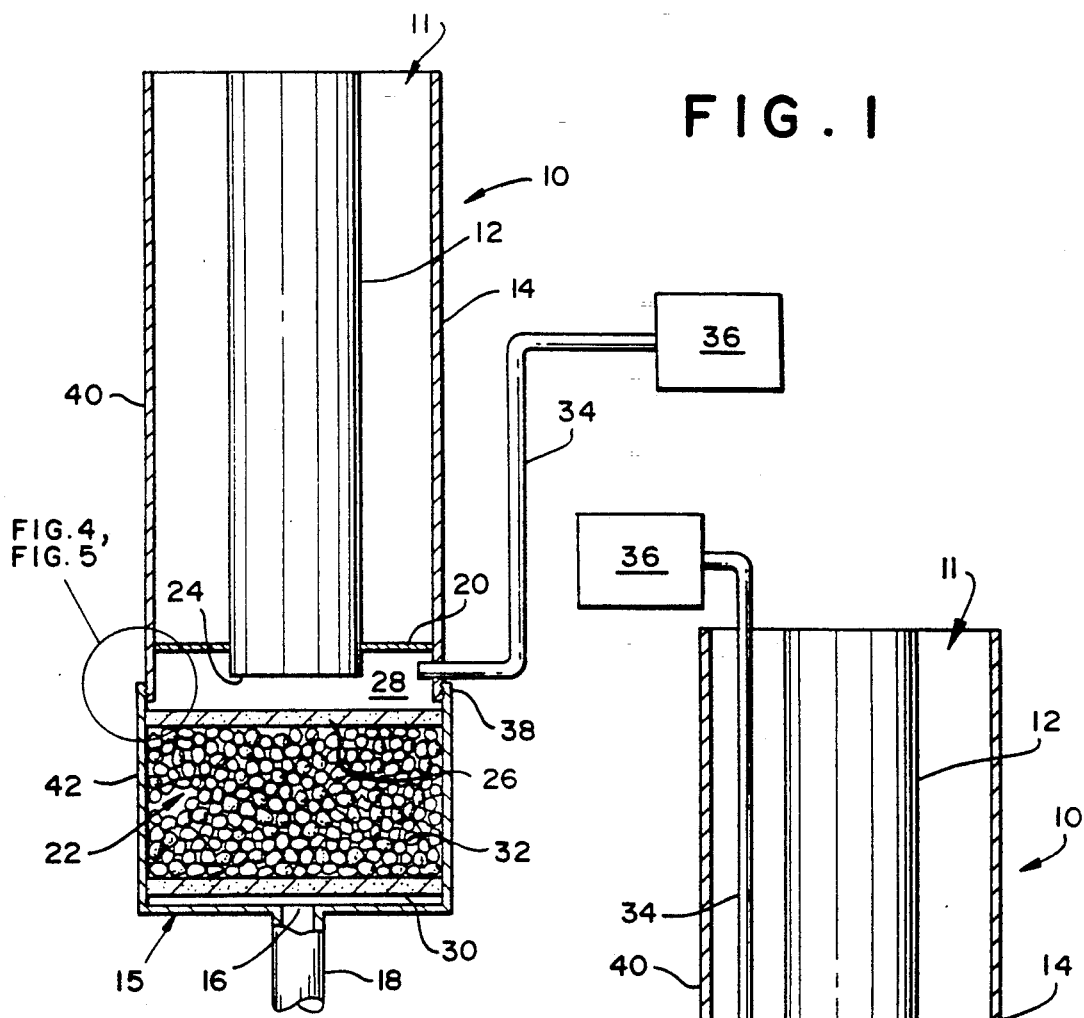

METHOD OF DETECTION USING SENSOR ELECTRODE

FIELD OF THE INVENTION

The present invention relates to a sensor electrode used to detect various select characteristics of a liquid. More specifically disclosed is an apparatus and method for protecting the sensor electrode from the harmful effects of undesirable contaminants in the liquid.

BACKGROUND OF THE INVENTION

Sensor electrodes are utilized to detect and monitor various characteristics of a liquid, both hydrocarbon and aqueous based. During the processing or monitoring of these liquids, it is desirable, if not essential, to be aware of characteristics such as acidity levels, conductivity and the amounts of specific ions such as, for example, calcium, chloride, bromide, ammonium, cupric, lead, sodium, nitrate and potassium, to name a few. Therefore, pH, conductivity, ORP and specific ion sensor electrodes are utilized.

In order for these selective sensor electrodes to function properly and give accurate, consistent results, a system of one or more filters may be employed to prevent contaminants from reaching the electrode and forming deposits on it or otherwise compromising its ability to function properly.

Filters are used to block dispersed solids. The filters may be designed in a variety of pore sizes and materials, depending upon the application. Pore sizes from 0.1 micron to 300 microns are typically used, although large pore sizes are not excluded depending on application. Filter materials may be constructed of sintered stainless steel, ceramics, teflon, cellulose, and other polymers.

Adsorbents are useful in blocking both particulate matter and various dissolved or discontinuous phase emulsified materials, such as oils (for aqueous liquids). The adsorbents may be utilized in a range of particle sizes and materials. The particle size employed will depend on the amount of material used in the adsorbent bed, as flow through the bed will be affected. Adsorbents utilized will be from a broad range of materials sold commercially for chromatographic applications. Typical materials which would be utilized include Tenax ®, Porapak, Amberlite ® XAD, activated carbon, selective ion exchange resins, etc.

Frequently, filters or adsorbents will incorporate specific activity in order to selectively remove certain dissolved compounds which, if allowed to reach the sensor electrode, would interfere with the electrode's ability to give an accurate reading of a desired compound or characteristic, because of its closely related chemical functionality to the interfering compound. Examples of such "interferences" include volatile amines for ammonia or the ammonium ion, volatile weak acids for carbon dioxide, chloride or bromide for the cupric ion, ammonium or silver for potassium and $Na^+$, $Cu^{++}$, $Zn^{++}$, $Fe^{++}$ and $Ni^{++}$ for water hardness readings. Even sodium (in basic solution) interferes with accurate pH readings.

Once the selective becomes saturated with its targeted contaminant, additional contaminant particles in the liquid sample will then proceed to clog it up by deposition or otherwise interfere with an accurate reading of the desired compound or characteristic. It is then necessary to remove and replace the saturated filter, resulting in undesirable downtime of the sensor system. In some instances, the sensor electrode may itself be so badly fouled or contaminated that it, too, must be removed and either manually cleaned or replaced with a new one.

Some sensor electrode systems employ a backflush feature, whereby the flow of filtrate is reversed through the filter or adsorbent to force the contaminants back out through the intake route. This theoretically regenerates the filter but is useful only when the contaminant is a solid. An example of such a device is the Filtrate Master System, sold by TBI-Bailey.

Where the contaminants are solubilized or, as with aqueous filtrates, oily compounds are present, backflushing with the filtrate being tested is generally ineffective. It is an object of this invention to prolong the life of the sensor electrode, provide more analytical accuracy and precision in the presence of interferences and to prolong the service life of the selective filters or adsorbents by removing specific interferents therefrom.

SUMMARY OF THE INVENTION

The invention involves filtration to remove solids or particulate material followed by contact with a regenerable adsorbent selected for its ability to remove the contaminants of interest while allowing the analyte of interest to remain in solution at its true concentration. The adsorbent and filter are periodically backflushed with a specifically tailored cleaning solution, thus regenerating both filter and adsorbent. The cleaners may be acidic, neutral, or basic. The cleaners may be aqueous or non-aqueous, and may or may not contain surfactants, organic solvents, chelants, etc.

BRIEF DESCRIPTION OF THE DRAWINGS

FIG. 1 is a cross-sectional view of an embodiment of the invention.

FIG. 2 is a cross-sectional view of another embodiment of the invention.

DETAILED DESCRIPTION OF THE INVENTION

Figure 3:
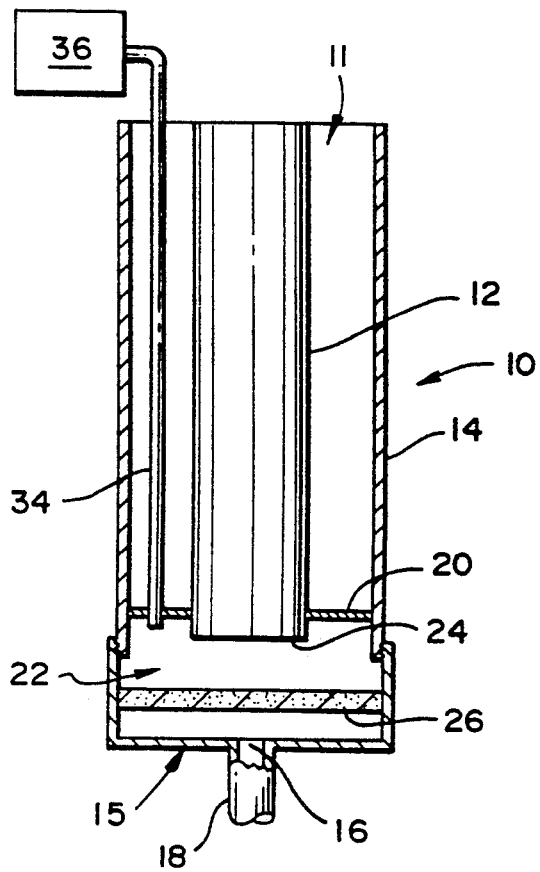
FIG. 3 is a cross-sectional view of an embodiment utilizing only a single filter.

The sensor electrode apparatus 10 of the present invention comprises a sensor electrode 12. The sensor electrode 12 is chosen as desired for its selectivity in detecting and measuring various characteristics in a liquid sample. Examples of the types of sensor electrodes which may be used in this invention are pH, conductivity, ORP and specific ion detectors. The specific ion sensor electrodes which may be selected include those which will detect ions such as, for example, calcium, chloride, bromide, ammonium, cupric, lead, sodium, nitrate and potassium.

The sensor electrode 12 is contained within a sensor electrode support housing 14 having a substantially cylindrical shape. The sensor electrode 12 is disposed generally through a first end 11 of the sensor electrode support housing 14. At the opposing or second end 15 of the sensor electrode support housing 14 is an opening 16 sealably engaged with a first conduit 18. An annular seal 20 is disposed inside the sensor electrode support housing 14 such that its outer perimeter forms a liquid impermeable seal with the inner wall of the sensor electrode support housing and its inner perimeter forms a liquid impermeable seal with the sensor electrode 12.

The area between the annular seal 20 and the second end 15 is defined as the liquid chamber 22. The portion of the sensor electrode that protrudes into the liquid chamber 22 is the sensing end 24. In one embodiment of the invention, as shown in FIGS. 1 and 2, a first filter 26, having a substantially disc-like shape, is disposed in proximity to the sensing end 24 and is in sealable engagement with the inner wall of the sensor electrode support housing 14. The area between the first filter 26 and the annular seal 20 is the liquid sample zone 28 of the liquid chamber 22. A second filter 30 is disposed in proximity to the second end 15 and is also in sealable engagement with the inner surface of the sensor electrode support housing 14. The area between the first filter 26 and the second filter 30 may contain adsorbent material or compounds, such as clays, activated carbon or selective ion exchange resins to form an adsorbent bed 32.

Adsorbents utilized are from a broad range of materials commercially available for chromatographic applications. The are sold under trade names such as Tenax ®, Porapak and Amberlite ® XAD. An alternative embodiment is shown in FIG. 3 wherein only one filter is utilized in the liquid chamber 22.

An alternative embodiment is shown in FIG. 3 wherein only a single filter is employed. Any of the embodiments shown in FIGS. 1, 2 and 3, or obvious variations thereof, are within the purview of the present invention.

A second conduit 34 terminates in the liquid sample zone 28 and is used to create a vacuum in the liquid sample zone 28 generated by a variable speed, reversible pump means 36. In operation, the liquid sample is drawn into liquid chamber 22 by the vacuum pressure generated by pump means 36.

As the liquid sample is drawn from the first conduit 18 through the filter, filters or adsorbent material specific contaminants are removed therefrom. This results in a substantially purified liquid reaching the liquid sample zone 28 containing only the characteristic, e.g., specific ion, pH or conductive elements, which is desired to be measured by the sensor electrode 12, without the presence of competing interferents.

Problems, arise, however, when the first filter, second filter or adsorbent bed, or combination thereof, is saturated with the contaminant or interferent it is designed to entrap. At this point, additional interferents or contaminants will pass through into the liquid sample zone and either cause the sensor electrode 12 to give inaccurate readings or to partially or completely foul the sensing end 24 of the sensor electrode 12. Before further sample testing can continue, the entire device must be disassembled to remove the saturated filters and/or adsorbent bed and install fresh filters or beds. In the worst case, and as often happens, the sensor probe is so badly contaminated that replacement of it is necessary.

The present invention substantially alleviates this problem by cleaning the saturated filter or adsorbent bed with a chemical solution selected to remove the specific contaminant. The solution is supplied to the liquid sample zone by pump means 36 via the second conduit 34 with sufficient pressure so as to back flush the filter or adsorbent bed to remove the contaminants or interferents therefrom. The contaminants or interferents are thereby forced out the first conduit 18. The cleansed filters and/or adsorbent bed is then ready to allow the sensor electrode to be used to test additional liquid samples.

The chemical solution is selected to cleanse the filter and/or adsorbent bed of a specific contaminant or contaminants. For example, if an aqueous liquid is being sampled and oil particles are an undesirable contaminant, then a reversed phase $C_{18}$ adsorbent chromatographic packing from Alltech Associates or other supplier may be used to adsorb the oil and prevent fouling of the sensor electrode. Periodically, based on experience with the level of oil contaminant, a chemical cleaning solution most suitable to back flush (desorb) the adsorbed oil from the reversed phase $C_{18}$ adsorbent would be employed. For example, such a solution may be aqueous methanol. Or, if humic acid contaminants are selectively removed by an adsorbent such as a macroreticular anion exchanger resin, in particular Amberlite ® IR 904/938 mixture, then in order to regenerate the anion exchange resin with contaminant cleaning/desorbing of humic acid contaminant, a 10% sodium chloride/1% sodium hydroxide water solution would be employed.

The back flushing step may be performed as often as needed. This will depend upon variables such as concentration of the contaminant in the liquid being tested, the activity level of the filter, filters and/or adsorbent bed and the sensitivity of the sensor electrode.

The sensor electrode apparatus of the present invention also comprises means 38 for separating the sensor electrode support housing into two pieces. Means 38 circumscribe the perimeter of the sensor electrode support housing 14 in proximity to the liquid sample zone 28. The first section 40 of the sensor electrode support housing 14 contains the sensor electrode 12 and the second section 42 of the sensor electrode support housing 14 contains the liquid chamber 22. Separation is necessary to provide for initial installation of the filter, filter and/or the adsorbent bed or to change from one specific contaminant selective filter to another.

Figure 5:
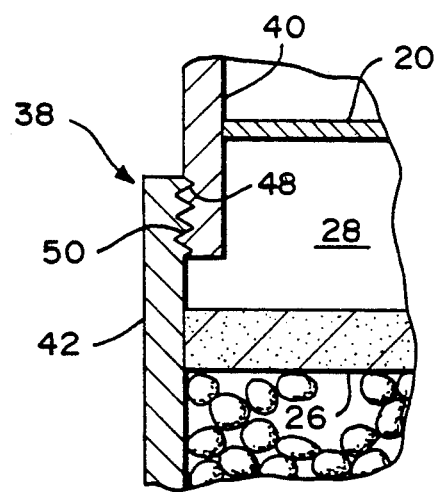
FIG. 5 is an enlarged cross-sectioned view of another embodiment of FIGS. 1, 2 and 3.
Figure 4:
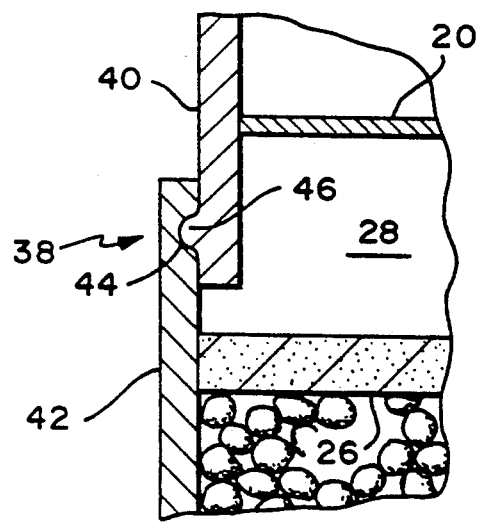
FIG. 4 is an enlarged cross-sectional view of a portion of FIGS. 1, 2 and 3.

FIG. 4 shows an embodiment of means 38 whereby an annular groove 44 in the internal surface of the wall of the second section 42 is securely fitted over a corresponding annular ridge 46 on the outer surface of the wall of the first section 40 in order to provide a liquid impermeable seal. An alternative, and more preferable, design is shown in FIG. 5 whereby screw threads 48 on the outer surface of the wall of the first section 0 are sealably engaged with screw threads 50 on the inner surface of the wall of the second section 42. Other means 38 are within the purview of the invention such that the two sections of the sensor electrode support housing may be sequentially separated and sealably reconnected as desired.

While the invention has been described with respect to particular embodiments thereof, it is apparent that numerous other forms and modifications will be obvious from this disclosure to those skilled in the art. The appended claims and this invention generally should be construed to cover all such obvious forms and modifications which are within the true spirit and scope of the present invention.

What I claim is:

1. A method for detecting selective characteristics of a liquid comprising drawing the liquid through a first filter, a second filter, an absorbent compound or any combination thereof to remove specific contaminants from the liquid into a liquid chamber which contains a sensor electrode and periodically backflushing the first filter, second filter, absorbent compound or any combination thereof with a cleaning solution selected to remove the specific contaminant from the first filter, second filter, absorbent compound or any combination thereof.

* * * * *